United States Patent [19]

Yasuda et al.

[11] 4,327,054

[45] Apr. 27, 1982

[54] GAS SENSOR ASSEMBLY

[75] Inventors: Eturo Yasuda, Okazaki; Minoru Ohta, Anjo, both of Japan

[73] Assignee: Nippon Soken, Inc., Nishio, Japan

[21] Appl. No.: 105,120

[22] Filed: Dec. 19, 1979

[30] Foreign Application Priority Data

Jan. 25, 1979 [JP] Japan .............................. 54-8492[U]

[51] Int. Cl.³ .............................................. G01N 27/12
[52] U.S. Cl. ..................................... 422/95; 73/27 R; 324/71 SN; 338/28; 338/34; 422/98
[58] Field of Search ..................................... 422/94–98; 324/65 R, 65 P, 71 R, 71 SN; 338/28, 34; 73/27 R

[56] References Cited

U.S. PATENT DOCUMENTS 4,234,542 11/1980 Romine .................................. 422/98
4,244,918 1/1981 Yasuda et al. ......................... 422/95

Primary Examiner—Arnold Turk
Attorney, Agent, or Firm—Cushman, Darby & Cushman

[57] ABSTRACT

A gas sensor assembly comprises first and second sinters each composed of a metal oxide having an electric resistance value varying in dependence on the composition of a detected gas as well as the detected gas temperature, and the first sinter has deposited thereon a catalyst for causing an oxidation reaction of the detected gas components. To detect a change in the electric resistance value of the first sinter which is temperature compensated by the second sinter, the first and second sinters are connected to each other with separated first and second electrodes so as to support the sinters in an opposing relation and a third electrode is connected to the second electrode in such a manner that the third electrode is apart from the first and second electrodes.

3 Claims, 8 Drawing Figures

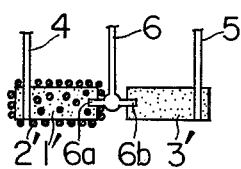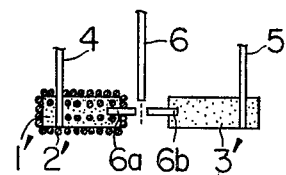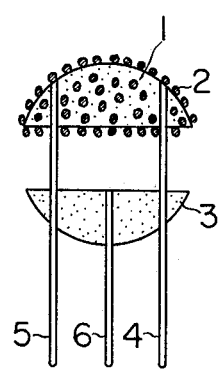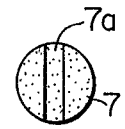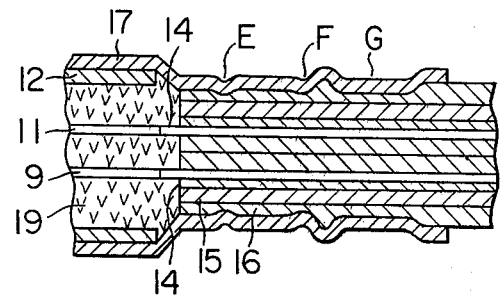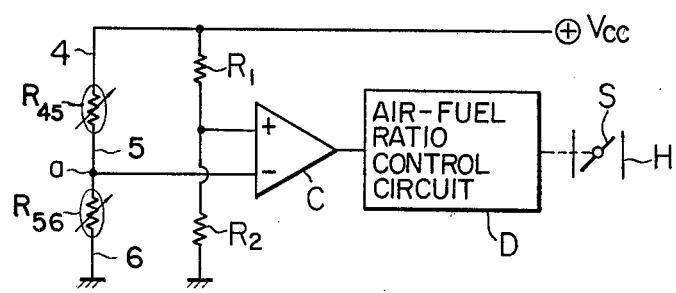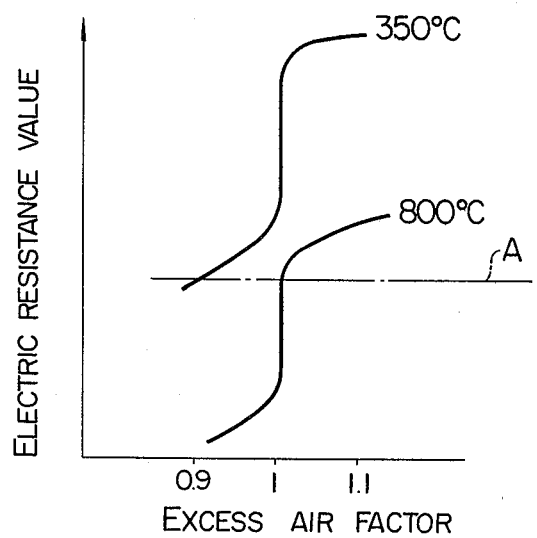

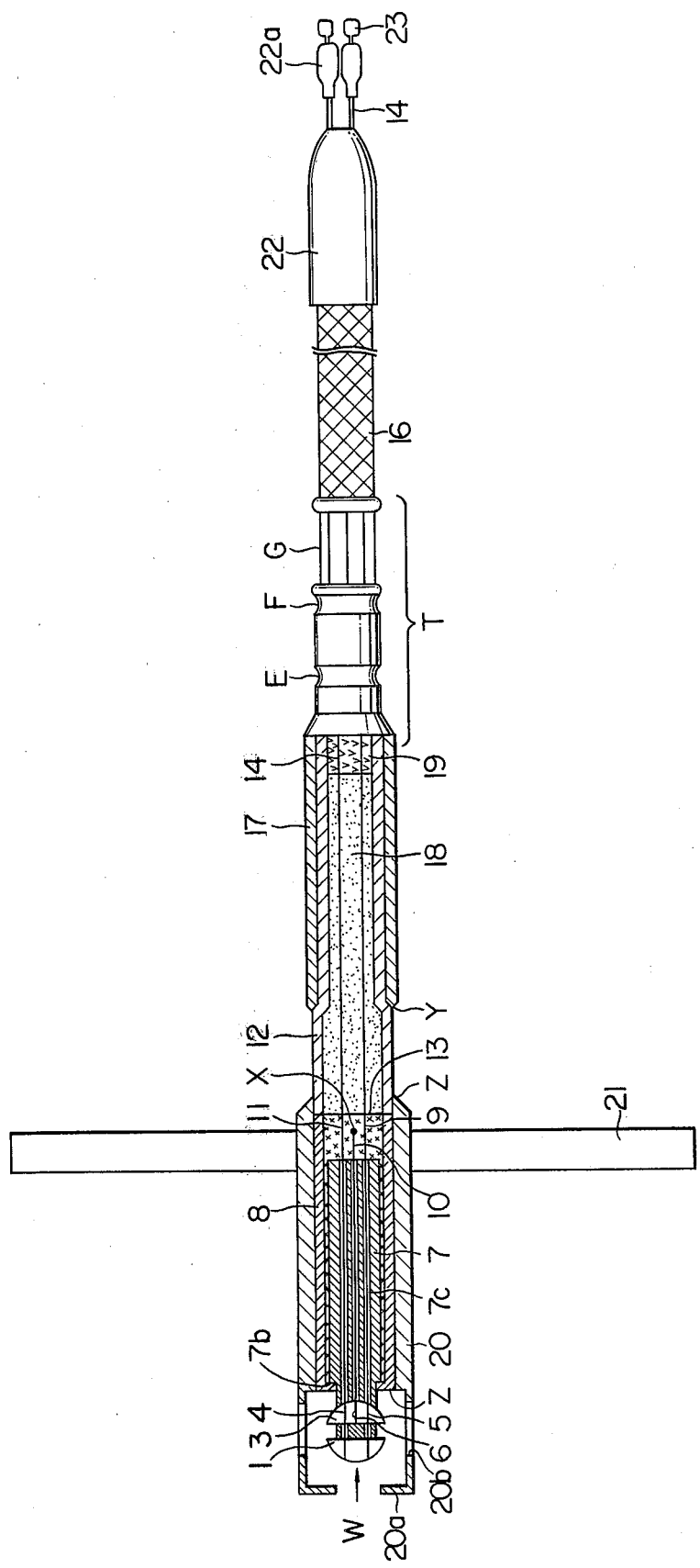

GAS SENSOR ASSEMBLY

BACKGROUND OF THE INVENTION

This invention relates to a gas sensor assembly for gas composition detectors of the type in which a change in the concentration of a gas component such as oxygen, carbon monoxide or hydrocarbon in the exhaust gases discharged from an internal combustion engine is detected as a change in the overall atmosphere.

In recent years, in connection with the control of exhaust emissions from internal combustion engines, gas composition detectors have been used as a means of detecting the air-fuel ratio of the mixture supplied for combustion in the engine.

More specifically, where an exhaust gas purifying catalyst is for example used as a means of controlling the exhaust emissions of an engine, in order that the catalyst may be allowed to perform its function as fully as possible, the air-fuel ratio of mixtures must always be maintained at the proper value and in the case of the carburetor in an ordinary engine or the injection system of a fuel injection type engine, the air-fuel ratio of mixtures tends in fact to vary greatly, even if the carburetor or the injection system is set so as to maintain the air-fuel ratio constant. As a result, in order to maintain the air-fuel ratio constant, it is necessary to detect the actual air-fuel ratio by some means or other and feed the detection signal back to the carburetor or the injection system.

The detection of air-fuel ratio by the gas composition detector is accomplished by directly utilizing the fact that a change in the concentration of any component of the exhaust gases is closely related to the air-fuel ratio of the mixture. In this case, the change in the temperature of the exhaust gases and the concentration change of the gas component occur abruptly and to a great extent and consequently there is a need for an accurate detector from the standpoint of this point.

In one of the known methods of detecting the air-fuel of the mixture supplied to an engine, a transition-metal oxide responsive to an exhaust gas component is used and a change in its electric resistance value is detected.

However, this method is disadvantageous in that since the electric resistance value of the transition-metal oxide varies in dependence on the concentration as well as the temperature of the exhaust gas component, while the air-fuel ratio of mixture can be controlled at the stoichiometric ratio when the temperature of the exhaust gases is held at 850° C., when the exhaust gas temperature is at 350° C. there is the danger of the air-fuel ratio being controlled at a rich ratio as compared with the stoichiometric ratio and thereby failing to control the air-fuel ratio at the stoichiometric ratio, with the result that it is impossible to accurately control the air-fuel ratio unless compensation is made for changes in the electric resistance due to changes in the temperature of the exhaust gases, namely unless temperature compensation is provided.

To overcome this deficiency, gas composition detectors have been proposed as disclosed, for example, in Japanese Laid-Open Patent Application No. 53-136898 and this type of known detector comprises two sintered bodies made of a metal oxide whose electric resistance value varies with the composition and temperature of exhaust gases and only one of the sintered bodies has deposited thereon a catalyst for oxidizing the gas components, whereby the electric resistance value of the catalyst-deposited sintered body is detected while providing the required temperature compensation by the other sintered body having no catalyst, thus detecting variation of the electric resistance value which is dependent only on the gas composition and not affected by the temperature of the exhaust gases and thereby accurately controlling the air-fuel ratio of mixtures.

A disadvantage of this type of known detector is that since the sintered bodies are interconnected with three electrodes which are welded together and the elements are arranged in parallel, the connections of the sintered bodies are not secure with the result that during handling of them the interconnected portion tends to be broken, causing damages to the sintered elements.

SUMMARY OF THE INVENTION

With a view to overcoming the foregoing deficiencies in the prior art, it is the object of the present invention to provide a gas sensor assembly comprising two sinters (sintered bodies) arranged opposite to each other and connected to each other with two electrodes which are separated from each other, a catalyst deposited on one of the sinters and another electrode separated from the two electrodes and connected to the other sinter having no catalyst, whereby the interconnection of the two sinters with the two electrodes results in a rugged construction and the danger of damages to the sensor assembly during the handling thereof is eliminated.

It is another object of the invention to provide an air-fuel ratio control circuit incorporating such gas sensor assembly.

BRIEF DESCRIPTION OF THE DRAWINGS

FIGS. 1A and 1B are sectional view showing the construction of a prior art gas sensor assembly.

FIG. 2 is a sectional view showing an embodiment of a gas sensor assembly according to the invention.

FIG. 3 is a partially sectional view showing an exemplary construction of a gas composition detector incorporating the gas sensor assembly of FIG. 2.

FIG. 4 is a plan view showing a ceramic body of FIG. 3 as looked in the direction of an arrow W in FIG. 3.

FIG. 5 is a sectional view showing the section T in FIG. 3.

FIG. 6 is a wiring diagram showing an embodiment of an air-fuel ratio detecting circuit incorporating the gas sensor assembly of FIG. 2.

FIG. 7 is a characteristic diagram useful for explaining the present invention and the prior art sensor assembly.

DESCRIPTION OF THE PREFERRED EMBODIMENTS

FIG. 1A is a sectional view showing the construction of a prior art gas sensor assembly, and FIG. 1B shows the manner in which the two sinters of the sensor assembly are connected to each other by welding the electrodes. In the Figures, numeral 1' designates one of the sinters constituting a first gas composition sensing element, 2' an oxidizing catalyst comprising platinum or the like, 3' the other sinter constituting a second gas composition sensing element, 4, 5 and 6 electrodes, and 6a and 6b electrode pieces connected to the electrode 6 by welding. More specifically, the gas sensor assembly is constructed by first preparing the sinters 1' and 3' having the platinum electrodes 4, 5, 6a and 6b attached thereto, depositing the catalyst 2' on the sinter 1' and then welding the electrode pieces 6a and 6b on the sinter and the electrode 6 together so as to connect the first and second sinters 1' and 2' in series as shown in FIG. 1A. This construction of the prior art assembly is disadvantageous in that since the two sinters are arranged in parallel spatially as mentioned previously, the mechanical strength of the connections are not firm and strong and thus during the handling of the assembly there is the danger of the connections of the sinters being broken and causing damages to them and the sensor assembly.

Referring to FIG. 2 showing an embodiment of the invention, numeral 1 designates a first sintered body composed of an oxide of titanium ($TiO_2$) and in the form of a semicircular plate. Since the first sinter 1 is made of $TiO_2$, its electric resistance values varies with the composition and temperature of exhaust gases.

Numeral 2 designates an oxidizing catalyst composed of a platinum-rhodium alloy which is deposited on both the outer and inner surfaces of the first sinter 1 to serve the function of subjecting the gas components around the first sinter 1 to oxidation reaction. Numeral 3 designates a second sinter comprising $TiO_2$ and taking the form of a semicircular plate. Numerals 4 and 5 designate heat and corrosion resistant electrodes made of platinum or platinum-rhodium. The first and second sinters 1 and 3 are arranged one over the other with their flat portions opposing each other and in this condition the electrodes 4 and 5 extend in a spaced relation through the sinters 1 and 3 to connect them with each other. Numeral 6 designates another electrode made of the same material as the electrodes 4 and 5 and inserted into the second sinter 3 so as to be apart from the electrodes 4 and 5.

Next, the manufacturing method of the sinters 1 and 3 will be described.

Powdered titanium oxide which has been presintered or calcined and stabilized at 1200° C. is crushed into small particles in a ball mill and then an organic binder such as polyvinyl alcohol is added to the particles to nodulize the same into nodules of about 30 to 80 mesh size. The nodules and platinum electrodes are compacted and molded integrally in a mold under a desired pressure and the resulting product is then fired for 2 hours at 1100° C. In this way, the required two sinters with electrodes are formed and only one of the sinters is dipped in an aqueous solution comprising 100 grams of platinic chloride acid and 11 grams of rhodium trichloride. The thus dipped sinter is dried and then fired for 2 hours at 800° C. In this way, the desired catalyst is carried by one of the sinters. The two electrodes of the respective sinters are connected by spot welding thus producing a gas sensor assembly of the construction shown in FIG. 2.

It should be noted that where it is desired to deposit the catalyst 2 on the first sinter 1 by this dipping process with the first and second sinters 1 and 3 being connected with the electrodes 4 and 5, if the spacing between the sinters 1 and 3 is very small, there will be an undesirable effect of applying the solution to the second sinter 3 by a capillary phenomenon. Of course, if the spacing between the sinters 1 and 3 is large enough or an evaporation process other than the dipping process is used, there will be no problem, even if the sinters 1 and 3 are preliminarily connected with the electrodes 4 and 5.

The construction of the invention shown in FIG. 2 has the advantage of the rugged construction due to the connection of the two sinters 1 and 3 with the two electrodes 4 and 5.

The functions of the first and second sinters 1 and 3 when placed in the exhaust gases of an engine will now be described. As is well known in the art, the exhaust gases comprising such components as $O_2$, $NO_x$, CO, HC and $H_2$ and the concentrations of these components vary with the air-fuel ratio of the mixture before burning. Generally, the gas sensing device has an electric resistance value corresponding not to changes in the partial pressure of the gas components but to a change in the overall atmosphere which is brought about by these changes and the electric resistance value also varies under the effect of the exhaust gas temperature. Due to the action of the catalyst 2, the first sinter 1 promotes such reactions as $CO + \frac{1}{2}O_2 \rightarrow CO_2$, and $HC + XO_2 \rightarrow YCO_2 + 2H_2O$, so that the partial pressure of $O_2$ in the reducing atmosphere and that of $O_2$ in the oxidizing atmosphere of the exhaust gases change abruptly at the surface of the first sinter 1 and the resulting abrupt change in the electric resistance value which occurs at the threshold point of stoichiometric air-fuel ratio is generated between the electrodes 4 and 5. On the contrary, the oxygen partial pressure does not vary abruptly at the surface of the second sinter 3 due to the absence of any catalyst. As a result, the electric resistance value does not vary to any great extent with the gas composition and the resistance value varies mainly with the temperature of the exhaust gases. Consequently, the electric resistance value depending on the composition and temperature of the exhaust gases is taken from between the electrodes 4 and 5 of the first sinter 1 and the electric resistance value depending on the exhaust gas temperature alone is taken from between the electrodes 5 and 6 of the second sinter 3. In this case, the rate of change with temperature of the electric resistance value between the electrodes 4 and 5 is equal to that of the electric resistance value between the electrodes 5 and 6 due to the fact that the first and second sinters 1 and 3 are composed of the metal oxide of the same composition. Thus, with the combination of the first and second sinters 1 and 3, a change in the electric resistance value of the first sinter 1 can be detected while providing the required temperature compensation by the second sinter 3 and thus the gas composition can be accurately detected irrespective of changes in the exhaust gas temperature.

Next, the overall construction of an exemplary gas composition detector incorporating the gas sensor assembly of the invention constructed as described above will be described with reference to FIGS. 3 to 5. In the Figures, numeral 7 designates a cylindrically ceramic body made of a material having a high electrical insulating property, such as aluminum oxide and the ceramic body 7 includes at its one end a groove 7a having a semicircular bottom and a stepped portion 7b located below the grooved end. The ceramic body 7 also includes three longitudinal holes 7c formed therethrough and spaced from one another. Numeral 8 designates a cylindrical tube of a heat resisting and corrosion resisting metal such as stainless steel and one end of the cylindrical tube 8 is fixedly secured to the stepped portion 7b of the ceramic body 7 by caulking. Numerals 9, 10 and 11 designate sublead wires each comprising a nichrome wire and the sublead wires 9, 10 and 11 are connected by welding to the electrodes 4, 5 and 6 of the first and second sinters 1 and 3. Of these sublead wires 9, 10 and 11, the sublead wire 10 connected to the electrode 6 is secured by welding to the inner side of the cylindrical tube 8 at a point X. Numeral 12 designates a cylindrical tube made of stainless steel and the cylindrical tube 12 is secured by welding to the cylindrical tube 8 over the entire end surface thereof. Numeral 13 designates a glass sealing compound in a fused and solidified state and the sealing compound 13 is provided to insulate and fix the sublead wires 9, 10 and 11 in place within the cylindrical tube 8 and also to prevent the leakage of the exhaust gases through the holes 7c of the ceramic body 7. Numeral 14 designates two stainless steel lead wires respectively connected electrically to the lead wires 9 and 11 and an outer cover 14a of the lead wire 14 is made of glass fiber. Numeral 15 designates a protective layer made of glass fiber applied to the outer surfaces of the outer covers 14a to combine the lead wires 14. Numeral 16 designates a metal layer made of stainless steel and wrapped around the outer surface of the protective layer 15. Numeral 17 designates a cylindrical tube made of stainless steel and fitted on the outer surface of the cylindrical tube 12 and these tubes are welded together over the entire circumference of a portion Y. The cylindrical tube 17 is also fitted to cover a portion of the outermost surface metal layer 16 of the lead wires 14 and the cylindrical tube 17 is not only mechanically caulked over the entire circumference at portions E and F but also mechanically caulked at eight points which are equispaced around the circumference of a portion G so as to tightly fit the stainless steel layer 16 to the inside of the cylindrical tube 17. Numeral 18 designates an electrical insulating compound made of magnesium oxide, for example, and the purpose of the electrical insulating compound 18 is to insulate and hold in place the sublead wires 9 and 11 which are inside the cylindrical tube 12. Numeral 19 designates a heat resisting rubber such as silicone rubber. Numeral 20 designates a stainless steel housing which is secured by welding to the cylindrical tube 12 over the entire circumference of portions Z and the housing 20 includes two radially inwardly extended bent portions 20a and two openings 20b for passing the exhaust gases. Numeral 21 designates a mounting flange made of stainless steel and secured by welding to the housing 20 so as to be fitted to the exhaust pipe (not shown). Numerals 22 and 22a designate heat-shrinkable tubes, and 23 connecting terminals.

An exemplary air-fuel ratio control circuit incorporating the gas composition detector of the above-described construction will now be described with reference to FIG. 6 in which the electrode 4 is connected to the positive terminal of a constant voltage source, the electrode 6 is grounded and the electrode 5 is connected to a point a. Reference numeral $R_{45}$ indicates the resistance of the first and second sinters (1,3) between electrodes 4 and 5, and reference numeral $R_{56}$ indicates the resistance of the second sinter (3) across electrodes 5 and 6. Thus, the respective electrodes are appropriately connected to take out at the intermediate point a a voltage dependent only on the concentration of the gas composition. The voltage at the intermediate point a is connected for example to the inverting input terminal of a comparator C and a preset voltage determined by series-connected fixed resistors $R_1$ and $R_2$ is applied to the non-inverting input terminal of the comparator C. At the intermediate point a, the change in the temperature-dependent electric resistance value appearing between the electrodes 4 and 5 and the change in the temperature-dependent electric resistance value appearing between the electrodes 5 and 6 practically cancel each other and consequently a voltage is generated at the intermediate point a which is practically related to the abrupt change in the electric resistance value depending on the gas composition and appearing between the electrodes 4 and 5. In other words, a voltage is generated at the intermediate point a which is dependent only on the concentration of the gas composition (or the air-fuel ratio). Thus, since the electric resistance value of the first sinter 1 varying with the gas composition abruptly changes at around the stoichiometric air-fuel ratio as a threshold, in order to control the air-fuel ratio of mixtures at the stoichiometric ratio, it is only necessary to apply the voltage corresponding to the stoichiometric ratio (shown by the dot-and-dash line A in FIG. 7) as a preset voltage to the positive input terminal of the comparator C.

The comparator C compares the input voltages and it applies an input signal to an air-fuel ratio control circuit D which in turn generates a signal for operating an actuator, such as a throttle valve S of a carburetor H. When, for example, the detected air-fuel ratio is lean as compared with the stoichiometric ratio so that the voltage at the intermediate point a becomes higher than the preset voltage, a signal is generated so that the actuator is operated so as to enrich the air-fuel ratio to approach the stoichiometric ratio. On the contrary, when the detected air-fuel ratio is rich as compared with the stoichiometric ratio so that the voltage at the intermediate point a becomes lower than the preset voltage, a signal is generated so that the actuator is operated so as to change the air-fuel ratio to a leaner value to approach the stoichiometric ratio.

As will be seen from the foregoing description, a change in the electric resistance value of the first sinter 1 can be detected while providing the required temperature compensation by means of the second sinter 3 and consequently substantially the accurate detection of air-fuel ratio can always be accomplished. It should be noted that in the gas sensor assembly of this invention the two sinters 1 and 3 are connected to each other with the two electrodes 4 and 5, with the result that in FIG. 6 either one of the electrodes 4 and 5 may be connected to either the positive terminal of the constant voltage source or the ground and consequently there is no need to make any distinction between the electrodes 4 and 5.

While, in the embodiment described above, the first and second sinters 1 and 3 are each composed of $TiO_2$ (titanium oxide), the sinters 1 and 3 may each be composed of $SnO_2$ (tin oxide) or a combination of different metal oxides having substantially the same activation energy of resistance-temperature characteristic, such as $ZrO_2$ (zirconium oxide), NiO (nickel oxide), $CeO_2$ (cerium oxide) and ZnO (zinc oxide).

On the other hand, the catalyst 2 need not be limited to those of the above-described embodiment, since it is possible to use any one of many other catalysts in addition to Pt and Pt-Rh.

Further, the shape of the first and second sinters 1 and 3 is not intended to be limited to the semicircular plate form and they may be formed into any other shape, such as a rectangular shape.

It will thus be seen from the foregoing description that in accordance with the invention, since a gas sensor assembly comprises a first sinter composed of a metal oxide having an electric resistance value varying with the composition and temperature of a detected gas and having deposited thereon a catalyst adapted for subjecting the detected gas components to oxidation reaction and a second sinter composed of a metal oxide having an electric resistance value varying with the composition and temperature of the detected gas and having deposited thereon no such catalyst as mentioned previously and since the sinters are not only arranged in an opposing relation but also connected to each other with two separated electrodes with another electrode separated from the two electrodes being connected to the second sinter, there is a great advantage that it is possible to detect an electric resistance value which is not dependent on the temperature but dependent on the composition of a detected gas as is the case with the prior art sensor assembly mentioned previously and it is thus possible to control the air-fuel ratio of mixtures accurately. Another great advantage is that the connection of the two sinters with the two electrodes separated from each other has the effect of making the assembly strong structurally and thereby preventing damages to the assembly during the handling thereof.

Still another advantage is that it is possible to connect and join two sinters with two electrodes without using such method as welding with the resulting simplification of the manufacture.

We claim:

1. A gas sensor assembly comprising:
    a first and a second sinter separated from each other by a space and each composed of a metal oxide having an electric resistance value varying in dependence on the composition and temperature of a detected gas, said first sinter having deposited thereon a catalyst for causing an oxidation reaction of the components of said detected gas;
    a first and a second electrode both of which extend through and are connected to both of said first and second sinters, respectively, to support the same in an opposing spaced relation; and
    a third electrode connected only to said second sinter in such a manner that said third electrode is apart from said first and second electrodes,
    whereby a change in the electric resistance value of said first sinter which is temperature compensated by said second sinter can be detected.

2. A gas sensor assembly according to claim 1, wherein each of said first and second sinters comprises a semicircular plate sinter having a straight lined side, and wherein said first and second electrodes support said semicircular plate sinters in such a manner that said sinters are arranged apart from each other with said straight lined sides facing each other.

3. A gas sensor assembly according to claim 1 or 2, further comprising a ceramic body having a groove and a stepped portion, said groove holding therein at least one of said first and second sinters, and comprising a cylindrical tube secured to said ceramic body at said stepped portion and having a glass sealing compound and an electrical insulating compound filled therein.

* * * * *